(12) United States Patent
Grotjahn et al.

(10) Patent No.: US 6,380,393 B1
(45) Date of Patent: Apr. 30, 2002

(54) LIGANDS, TRANSITION METAL COMPLEXES AND METHODS OF USING SAME

(75) Inventors: Douglas Bryan Grotjahn; David Combs, both of San Diego, CA (US)

(73) Assignee: San Diego State University Foundation, San Diego, CA (US)

( * ) Notice: Subject to any disclaimer, the term of this patent is extended or adjusted under 35 U.S.C. 154(b) by 0 days.

(21) Appl. No.: 09/273,082

(22) Filed: Mar. 19, 1999

(51) Int. Cl.[7] .......................... C07F 19/00; A61K 33/24; C07D 403/02
(52) U.S. Cl. ..................... 548/101; 424/617; 548/112; 548/365.1; 548/373.1; 548/375.1; 548/376.1; 548/377.1
(58) Field of Search .............................. 548/101, 365.1, 548/373.1, 375.1, 376.1, 377.1, 112; 424/617

(56) References Cited

U.S. PATENT DOCUMENTS

| | | |
|---|---|---|
| 5,159,099 A | 10/1992 | Romano et al. |
| 5,206,409 A | 4/1993 | Romano et al. |
| 5,597,942 A | 1/1997 | Pohl et al. |
| 5,599,994 A | 2/1997 | Pal et al. |
| 5,621,156 A | 4/1997 | Benham et al. |
| 5,624,969 A | 4/1997 | Seifert et al. |
| 5,663,064 A | 9/1997 | Burke et al. |
| 5,684,092 A | 11/1997 | Seifert et al. |
| 5,684,212 A | 11/1997 | Patton et al. |
| 5,705,078 A | 1/1998 | Kurek et al. |
| 5,719,273 A | 2/1998 | Tu et al. |
| 5,723,663 A | 3/1998 | Jackson et al. |
| 5,739,022 A | 4/1998 | Burstyn et al. |
| 5,741,955 A | 4/1998 | Beatty |
| 5,760,275 A | 6/1998 | Lassila |
| 5,763,652 A | 6/1998 | Kawabe et al. |
| 5,763,716 A | 6/1998 | Benham et al. |
| 5,817,636 A | 10/1998 | Eckstein et al. |
| 5,817,872 A | 10/1998 | Honda et al. |
| 5,820,840 A | 10/1998 | Horn Feja et al. |
| 5,821,553 A | 10/1998 | Evans et al. |
| 5,837,855 A | 11/1998 | Chowrira et al. |
| 5,840,500 A | 11/1998 | Pei et al. |

OTHER PUBLICATIONS

Cano, M. et al.: 3–[4–phenoxyphenyl]pyrazole (Hpz) and 3–[4–butoxyphenyl ]pyrazole (Hpz) in rhodium chemistry. J. Organomettal. Chem. vol. 534, pp. 159–172, 1997.*

M.T. Alonso et al, Journal of Organometallic Chemistry, 430 (1992) 335–347.
Deters et al, Inorganic Chimica Acta, 269 (1998) 117–124.
Kovari et al, Chem. Ber. (1994) 127, 2151–2157.
Meyer et al, Chem. Ber. (1997) 130, 605–613.
Katritzky et al, J. Org. Chem. (1988) 53, 5685–5689.
Begtrup, Acta Chemica Scandinavica 46 (1992) 972–980.
Rheingold et al, Inorg. Chem. (1998) 37, 3471–3477.
Singh et al, Inorg. Chem. (1998) 37, 1073–1079.
Konrad et al, J. Chem. Soc. Dalton Trans. (1988) 199–205.
Meyer et al., J. Chem Soc., Dalton Trans. (1998) 1181–1186.
Cheng et al, J. Chem. Soc. (1998) 120, 11018–11019.
Zadykowicz et al., J. Org. Chem. (1998) 63, 235–240.
Krooglyak et al., Inorg. Chem. (1996) 35, 4804–4806.
Comprehensive Coordination Chemistry, 2, 1987, p. 310.
Kovari et al, J. Am. Chem. Soc. (1996) 118, 12704–12709.
Zhu et al., J. Am. Chem. Soc. (1993) 115, 4566–4570.
Parac et al., J. Am. Chem. Soc. (1996) 118, 5946–5951.
Kaminskaia et al, Inorg. Chem. (1998) 37, 4302–4312.
Redmore et al, Inorg. Chem. (1997), 36, 4743–4748.
Van et al, Abstract of II Symposium Internacional: Investigation Quimica En La Frontera 12.9.98.
Satake et al, J. Am. Chem. Soc. (1998), 120, 10391–10396.
Schenck et al, Inorg. Chem. (1985) 24, 2334–2337.
Meyer et al, Chem. Ber./Recueil (1997) 130, 1441.
Jones, R.G., J. Am. Chem. Soc. (1949) 3994–4000.
Tokunga et al., Angew. Chem. Int. Ed. (1998), 37, No. 20, pp. 2867–2869

* cited by examiner

Primary Examiner—Charanjit S. Aulakh
(74) Attorney, Agent, or Firm—Stout, Uxa, Boyan & Mullins, LLP; Frank J. Uxa

(57) ABSTRACT

Compositions including at least one organic ligand including a first hetero atom and a second hetero atom directly bonded to the first hetero atom or located one carbon atom away from the first hetero atom, with at least one of the hetero atoms being nitrogen, and a transition metal moiety partially complexes by the organic ligand are provided. Such complexes have a controlled adaptable proton transfer ability and/or a hydrogen bonding ability which makes such compositions particularly useful as chemical reaction facilitators. Examples of chemical reactions facilitated by such compositions include hydrolysis reactions and carbon dioxide conversion reactions.

20 Claims, No Drawings

LIGANDS, TRANSITION METAL COMPLEXES AND METHODS OF USING SAME

BACKGROUND OF THE INVENTION

The present invention relates to ligands, transition metal complexes including such ligands and methods of using such ligands and complexes. More particularly the invention relates to ligands including first and second hetero atoms, transition metal complexes of such ligands in which only one of the first and second hetero atoms are directly bonded to the metal moiety and methods of using such ligands and complexes, for example, to facilitate chemical reactions, such as hydrolysis, alcoholysis and aminolysis reactions and carbon dioxide conversion reactions.

Medicinal chemists and biochemists want to know how amino acids are arranged in proteins, so that they can better understand the correlation between structures and the functions of drugs. One of the techniques used to accomplish the task of protein structure determination requires the breaking of amide bonds to liberate the amino acids. However, at physiological temperatures and pH 9, it takes an impractical length of time, for example, 168 years, to break half the amide bonds in a sample. In contrast, organisms found in nature have remarkably efficient systems to make and break amide bonds. Scientists have used natural enzymes such as carboxypeptidase to do the task of amide bond cleavage In some cases it is believed the crucial step involves proton transfer between imidazole, a carboxylate, and the amide undergoing hydrolysis while other enzymatic systems involve a metal catalyzed amide bond cleavage such as that seen in the zinc(II)-metalloprotease. However, the available enzymatic systems can be very complicated and sometimes difficult to handle due to their sensitivity to temperature and pH.

Catalysis of amide hydrolysis has been catalyzed not only by enzymes, but also by acids, bases, and metal ions. These systems take advantage of one or more possible factors which facilitate amide bond cleavage. First, the amide bond cleaving reagent or catalyst could act as a proton transfer reagent which can be an important factor in amide bond hydrolysis. Secondly, a metal may catalyze or mediate amide hydrolysis by acting as a Lewis acid through O-complexation, delivery of a metal coordinated hydroxide or a combination of the latter two processes.

Considerable work has been directed toward studying the amide hydrolysis reaction and the development of reagents which assist amide hydrolysis. Some work toward the development of an amide hydrolysis catalyst has been published by Kostic. For example, Kostic and coworkers have found that a palladium(II) complex can accomplish the hydrolysis of a number of dipeptides, but with only a modest 4 catalytic turnovers.

It would be advantageous to provide reaction facilitators, e.g., catalysts, promoters and the like, that mimic enzymatic systems in their hydrogen-bonding and/or proton transfer abilities, but are robust, simple to handle, and have useful reactor facilitation.

Industrial hydrolysis of acrylonitrile is used to make acrylic acid which, in turn, can be converted to a variety of esters such as methyl, ethyl, butyl, and 2-ethylhexyl acrylates. The acrylates can then be used as comonomers with methyl methacrylate and/or vinyl acetate to give polymers for water-based paints, among other products A number of industrial methods exist for obtaining acrylic acids from nitriles and one of the more economical methods is the direct hydrolysis of the acrylonitrile to the acrylic acid. However, this synthetic route involves the use of a stoichiometric amount of sulfuric acid to produce the acrylamide sulfate which is then treated with an alcohol to give the acrylic ester. It would be advantageous to provide a direct route from the acrylonitrile and alcohol to yield the desired acrylate without the need to use and then neutralize a strong acid As petroleum resources dwindle and the need to control the emissions of carbon dioxide into the environment increases, use of carbon dioxide as a feedstock becomes more desirable. It would be advantageous to provide materials useful to facilitate carbon dioxide conversion, for example, to carbonates, carbamates and ureas.

SUMMARY OF INVENTION

New ligands, transition metal complexes including such ligands and methods for using such ligands and complexes have been discovered. The present ligands and transition metal complexes can be produced using relatively straight-forward synthetic chemistry techniques. Moreover, the structures of the present ligands and metal complexes can be effectively selected or even controlled, for example, in terms of proton transfer ability and/or hydrogen bonding ability, thereby providing ligands and complexes with properties effective to facilitate one or more chemical reactions. Thus, the present metal complexes can be effectively used to facilitate, for example, catalyze, promote and the like, various chemical reactions, such as hydrolysis, alcoholysis and aminolysis reactions and carbon dioxide conversion reactions, which provide useful benefits. The present ligands and complexes have one or more other advantageous properties or characteristics which enhance their production and/or usefulness.

In one broad aspect of the present invention, compositions are provided which comprise at least one organic ligand and a transition metal moiety partially complexed by the organic ligand.

The present organic ligands, many of which themselves are novel and within the scope of the invention, include a first hetero atom and a second hetero atom directly bonded to the first hetero atom or located one carbon atom away from the first hetero atom. When the present organic ligands are complexed to the transition metal moiety, only one of the first and second hetero atom is directly bonded to the transition metal moiety, with the other of the first and second hetero atoms not being directly bonded to another transition metal moiety or being directly bonded to H (hydrogen atom). In addition, in the event the first and second hetero atoms are nitrogen and are located in a heterocycle and the organic ligand includes only a single additional hetero atom separated from the first or second hetero atoms by one or two carbon atoms, then the additional hetero atom is not included in an additional heterocycle. Also, if the organic ligand includes more than four hetero atoms, then the organic ligand includes at least one hetero atom other than nitrogen bonded directly to two (or more) other atoms. Alternately, if the organic ligand includes two pyrazole rings and at least two hetero atoms in the group connecting the two rings, then the organic ligand includes at least one hetero atom other than nitrogen.

In another embodiment, compositions within the scope of the present invention include an organic ligand having the following structure:

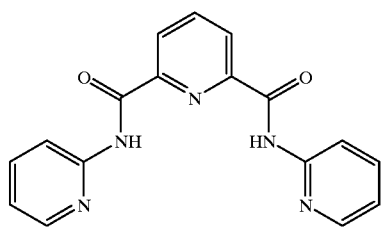

wherein the carbon atoms ortho to the nitrogen atoms in the two pendant heterocycles are bonded to a substituent other than —CH$_3$ (methyl); and a transition metal moiety partially complexed by the organic ligand.

In an additional embodiment, the present compositions include an organic ligand having the following structure:

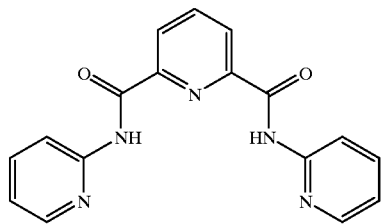

The transition metal moiety partially complexed with this organic ligand preferably is other than ruthenium.

The present organic ligands can be very effectively structured and adapted to control the proton transfer ability and/or hydrogen bonding ability of the transition metal complex of which the ligand is a part. In other words, the present ligands can be selected to obtain the desired degree of proton transfer ability and/or hydrogen bonding ability so that the resulting transition metal complex is highly effective in the desired application, for example, in facilitating a particular or specific chemical reaction. Such adaptability is very useful in providing the proper or desired degree of proton transfer and/or hydrogen bonding to achieve the desired degree of facilitation of a number of important chemical reactions, for example, hydrolysis, alcoholysis and aminolysis reactions, carbon dioxide conversion reactions, and reactions of alkenes or alkynes with water, alcohols, ammonia or amines.

In another broad aspect of the present invention, methods for producing a hydrolysis product are provided. Such methods comprise contacting a hydrolysis reactant in the presence of a composition in accordance with the present invention in an amount effective to facilitate the hydrolysis of the hydrolysis reactant to the hydrolysis product. This contacting occurs at effective hydrolysis conditions.

In yet another broad aspect of the present invention, methods for producing an alcoholysis product are provided. Such methods comprise contacting an alcoholysis reactant in the presence of a composition in accordance with the present invention in an amount effective to facilitate the alcoholysis of the alcoholysis reactant to the alcoholysis product This contacting occurs at effective alcoholysis conditions.

In one other broad aspect of the present invention, methods for producing an aminolysis product are provided. Such methods comprise contacting an aminolysis reactant in the presence of a composition in accordance with the present invention in an amount effective to facilitate the aminolysis of the aminolysis reactant to the aminolysis product. This contacting occurs at effective aminolysis conditions.

In a further broad aspect of the present invention, methods for converting carbon dioxide are provided. Such methods comprise contacting carbon dioxide in the presence of a composition in accordance with the present invention in an amount effective to facilitate the conversion of the carbon dioxide to a conversion product. The contacting occurs at effective carbon dioxide conversion conditions. The conversion product preferably is selected from ureas, carbamates and carbonates.

In an additional broad aspect of the present invention, methods for reacting alkenes or alkynes with water, alcohols, ammonia or amines are provided. Such methods comprise contacting the reactants in the presence of a composition in accordance with the present invention in an amount effective to facilitate the desired reaction to one or more desired products. The contacting occurs at effective reaction conditions.

Each feature and combination of two or more features described herein are included within the scope of the present invention provided that any two features of any such combination are not mutually inconsistent or incompatible.

These and other aspects and advantages of the present invention are set forth in the following detailed description, examples and claims.

DETAILED DESCRIPTION

In one aspect, the present invention is directed to organic ligands including a first hetero atom and a second hetero atom directly bonded to the first hetero atom or located one carbon atom away from the first hetero atom Examples of hetero atoms include nitrogen atoms (N), oxygen atoms (O), sulfur atoms (S) and phosphorus atoms (P). At least one of the first and second hetero atoms is, preferably both the first and second hetero atoms are, nitrogen.

When the present organic ligands are complexed to the transition metal moiety, only one of the first and second hetero atoms is directly bonded to the transition metal moiety. The other of the first and second hetero atoms is not directly bonded to another transition metal moiety or is directly bonded to H (hydrogen atom). In the event both the first and second hetero atoms are nitrogen and are located in a heterocycle and the organic ligand includes only a single additional hetero atom separated from the first or second hetero atoms by one or two carbon atoms, then the additional hetero atom is not included in an additional heterocycle. Also, if the organic ligand includes more than four hetero atoms, then the organic ligand includes at least one hetero atom other than nitrogen bonded directly to two (or more) other atoms. Alternately, if the organic ligand includes two pyrazole rings and at least two hetero atoms in the group connecting the two rings, then the organic ligand includes at least one hetero atom other than nitrogen.

In one embodiment, the organic ligand includes a heterocycle, for example, including at least one or two carbon atoms, with both the first and second hetero atoms located in the heterocycle. The organic ligand may include a single additional hetero atom separated from the heterocycle by one or two carbon atoms. This single additional hetero atom preferably is not located in an additional heterocycle. The additional hetero atom preferably is bonded, that is directly bonded, to a carbon atom of the heterocycle.

In one very useful embodiment, the other of the first and second hetero atoms is directly bonded to H. The feature of the present invention enhances the opportunity of hydrogen bonding in the present transition metal complexes. More preferably, the other of the first and second hetero atoms is not directly bonded to another transition metal moiety and is directly bonded to H The organic ligand may further include a third hetero atom located in a side chain bonded to the heterocycle including the first and second hetero atoms. The side chain may be bonded to the heterocycle at a carbon atom bonded directly to the first hetero atom. Alternately, the side chain may be bonded to one of the first and second hetero atoms. The side chain preferably includes one or two carbon atoms between the hererocycle and the third hetero atom.

One useful embodiment provides that the first and second hetero atoms are nitrogen atoms and the third hetero atom is selected from sulfur atoms, oxygen atoms and phosphorus atoms.

The organic ligands may include an additional heterocycle including one or two or more additional is hetero atoms. For example, the additional heterocycle may include a fourth hetero atom and a fifth hetero atom bonded to the fourth hetero atom or located one carbon atom away from the fourth hetero atom. The third hetero atom preferably is located in an additional side chain bonded to the additional heterocycle. Preferably, only one of the additional hetero atoms in the additional heterocycle, for example, only one of the fourth and fifth hetero atoms, is directly bonded to the transition metal moiety and the other additional hetero atom or atoms, for example, the other of the fourth and fifth hetero atoms, is (are) bonded directly to H.

Very useful organic ligands in accordance with the present invention are selected from the following:

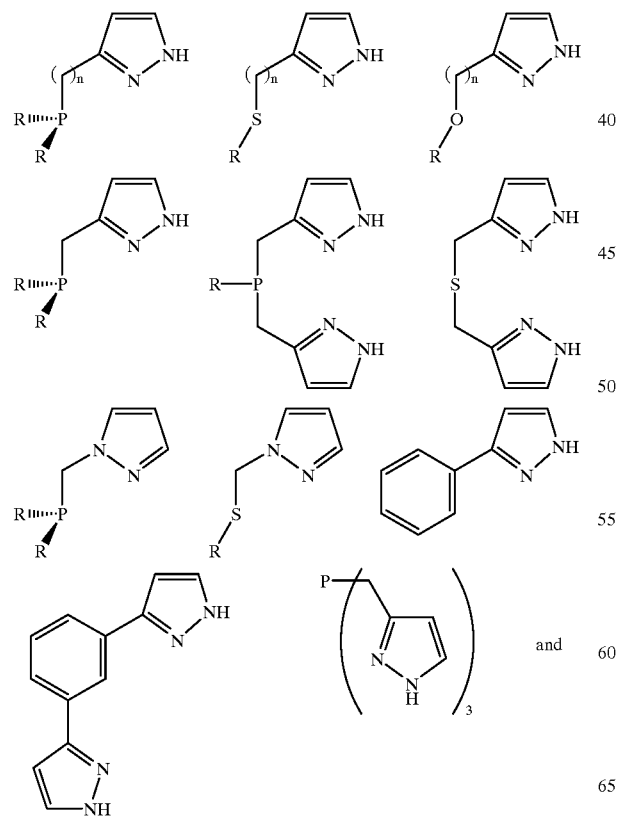

-continued

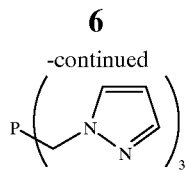

where n is an integer independently selected from one or two, and each R is independently selected from monovalent radicals, preferably monovalent substantially hydrocarbyl radicals.

Additionally, organic ligands in accordance with the present invention may be selected from:

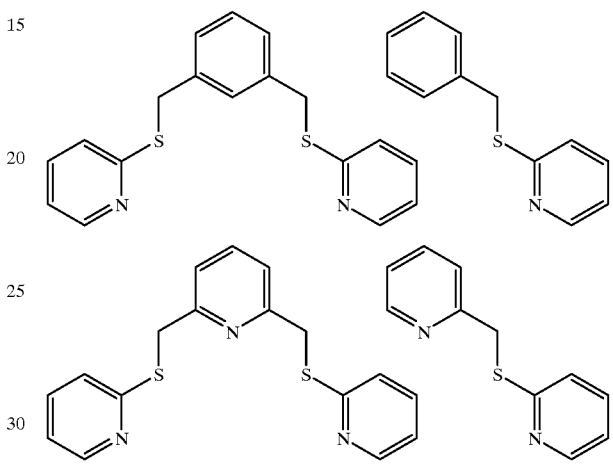

and all similar structures wherein the

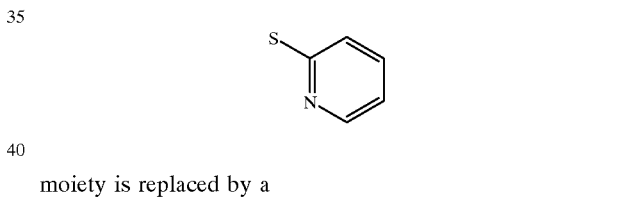

moiety is replaced by a

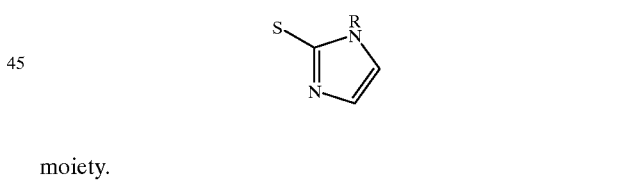

moiety.

Still further, the present organic ligands may be selected from

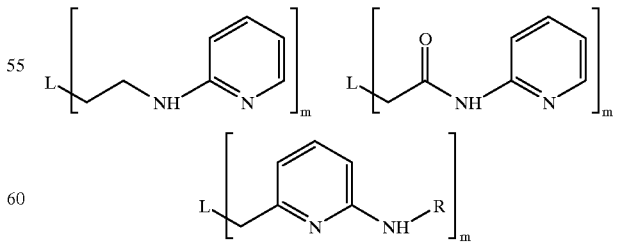

where L is selected from S, NH, NR, P, N, SR, PR and $PR_2$, m is an integer selected from 1, 2 or 3 and each R is independently selected from monovalent radicals, preferably monovalent substantially hydrocarbyl radicals.

In another embodiment, the organic ligand has the following structure:

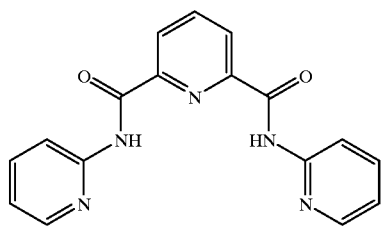

wherein the carbon atoms ortho to the nitrogen atoms in the two pendant heterocycles are bonded to a substituent other than —$CH_3$ (methyl).

In a still further embodiment, the organic ligand has the following structure:

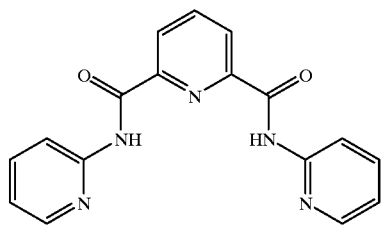

provided that the ligand is partially complexed to a transition metal moiety, as described elsewhere herein, other than a ruthenium moiety.

The transition metal moiety is partially complexed by at least one of the present organic ligands. The transition metal moiety may be a moiety of a metal selected from Group IB metals, Group IIB metals, Group IIIB metals, Group IVB metals, Group VB metals, Group VIB metals, Group VIIB metals and Group VIIIB metals. Preferably, the transition metal moiety is a moiety of a metal selected from chromium, manganese, iron, cobalt, nickel, copper, zinc, molybdenum, ruthenium, rhenium, palladium, silver, hafnium, tantalum, tungsten, rhodium, osmium, iridium, platinum and gold. Still more preferably, the transition metal moiety is a moiety of a metal selected from iron, cobalt, nickel, copper, zinc and palladium.

The present transition metal complexes preferably are soluble in the liquid medium in which such complexes are present or are used. The organic ligands may include one or more substituents, for example, one or more polar substituents and/or non-polar substituents, effective to increase the solubility of the ligand/transition metal complex in a given liquid medium. In addition, the present compositions may include one or more other or additional components, such as silver or thallium salts, acids, bases and the like, in an amount effective to interact with or otherwise affect the complex, for example, to activate the complex and/or to enhance the activity of the complex to facilitate a desired chemical reaction.

The present invention includes within its scope the present ligands and complexes as described herein and any and all substituted counterparts thereof. For example, unless otherwise expressly disclosed to the contrary, one or more of the hydrogen (H) substituents included in the present ligands can be replaced by another monovalent radical. Such substituted ligands, as well as the ligands with the hydrogen substituents, are included within the scope of the present invention.

In addition, any and all isomers, tautomers, enantiomers, and mixtures thereof of the present ligands are included within the scope of the present invention.

Examples of monovalent radicals which may be included as substituents in the present ligands, for example, as the R groups, include, but not limited to, monovalent hydrocarbon or hydrocarbyl groups, such as alkyl, alkenyl, alkynyl, aryl, alkyl aryl, alkenyl aryl, alkynyl aryl, aryl alkyl, aryl alkenyl, aryl alkynyl and cyclic monovalent hydrocarbon groups; halo such as F, Cl, Br and I; $NH_2$; $NO_2$; alkoxy; alkylthio; aryloxy; arylthio; alkanoyl; alkanoyloxy; aroyl; aroyloxy; acetyl; carbamoyl; alkylamino; dialkylamino; arylamino; alkylarylamino; diarylamino; alkanoylamino; alkylsulfinyl; alkylsulfenyl: alkylaulfonyl; alkylsulfonylamido; azido; benzyl; carboxy; cyano; guanyl; guanidino; imino; phosphinyl; silyl; thioxo; uredido or vinylidene or where one or more carbon atoms are replaced by one or more other species including, but not limited to, N, O, P, or S. The term "substantially hydrocarbyl radical" as used herein refers to a radical in which the number of carbon and hydrogen atoms are at least about 50%, and preferably at least about 70%, or at least about 80%, of the total number of atoms in the radical.

The present invention includes methods for producing a hydrolysis product. Such methods comprise contacting a hydrolysis reactant in the presence of a composition in accordance with the present invention in an amount effective to facilitate the hydrolysis of the hydrolysis reactant to the hydrolysis product. This contacting occurs at effective hydrolysis conditions. Such hydrolysis reaction conditions vary widely depending on many factors, such as the reactants and complex being employed, the concentrations of the reactants and complex, the desired product and other factors. However, such reaction conditions are not of critical importance in the present invention and may be selected from conditions conventionally used in similar reactions. Therefore, a detailed presentation of such conditions is not set forth herein.

The hydrolysis reactant preferably is selected from compounds including amide bonds, nitriles, phosphate esters, and cyanide ions.

Compounds including amide bonds which may be hydrolyzed in accordance with the present invention include, but are not limited to, formamide, acetamide, N-methylacetamide, N,N-dimethylacetamide, N,N-diethylacetamide, propionamide, N-methylpropionamide, is N,N-dimeethylpropionamide, N,N-diethylpropionamide, butyramide, N-methylbutyramide, N,N-dimethylbutyramide, acrylamide, N-methylacrylamide, N,N-dimethylacrylamide, benzamide, N-methylbenzamide, N,N-dimethylbenzamide, N,N-diethylbenzamide, o-, m-, and p-toluamides and their N-alkylated derivatives, acetanilide, o-, m-, and p-acetotoluidides, 2-acetamidophenol, 3-acetamidophenol, 4-acetamidophenol, N-acylated amino acids, glycylglycine, alanylalanine, and other polypeptides and proteins.

Nitriles which may be hydrolyzed in accordance with the present invention include, but are not limited to, linear or branched saturated alphatic $C_2$–$C_{18}$ mono- and $C_3$–$C_{19}$ dinitriles and phenyl derivatives thereof, $C_7$–$C_{13}$ saturated alphatic mono- and $C_5$–$C_{14}$ dinitriles, $C_3$–$C_{18}$ linear or branched olefinically unsaturated alphatic nitriles, $C_6$–$C_{13}$ olefinically unsaturated alicyclic nitriles, $C_7$–$C_{14}$ aromatic mono- and dinitriles $C_6$–$C_8$ heterocyclic nitrogen and oxygen mononitriles, $C_3$–$C_4$ cyanoalkanoic amides, $C_2$–$C_{12}$ saturated aliphatic cyanohydrins or hydroxynitriles, and mixtures of the above-described nitriles.

Specific examples include, but are not limited to, acetonitrile, propionitrile, buytronitrile, acrylonitrile, benzonitrile, and substituted derivatives Phosphate esters which may be hydrolyzed in accordance with the present invention include, but are not limited to, trialkyl phosphates, triaryl phosphates, dialkyl aryl phosphates, alkyl diaryl phosphates, dialkyl phosphates including DNA and RNA derivatives, diaryl phosphates, alkyl aryl phosphates, alkyl phosphates, aryl phosphates, and analogous phoshonic acid derivatives.

Further, the present invention includes methods for converting carbon dioxide. Such methods comprise contacting carbon dioxide in the presence of a composition in accordance with the present invention in an amount effective to facilitate the conversion of the carbon dioxide to a conversion product. The contacting occurs at effective carbon dioxide conversion conditions. Such reaction conditions vary widely depending on many factors, such as the complex being employed, concentrations of the carbon dioxide and complex, the desired product and other factors. However, such conditions are not critical in the present invention and may be selected from conditions conventionally utilized in similar carbon dioxide conversion reactions. Therefore, a detailed presentation of such conditions is not set forth here.

The carbon dioxide conversion product preferably is selected from ureas, carbamates and carbonates.

Another group of chemical reactions facilitated by the present metal complexes is illustrated by the reaction of alkenes with water to produce the corresponding alcohol.

Without wishing to limit the invention to any particular theory of operation, it is believed chat the reaction between water and ethylene can be facilitated using the present metal complexes in accordance with the mechanism given below:

tion conditions are not of critical importance in the present invention and may be selected from conditions conventionally used in similar reactions. Therefore, a detailed presentation of such conditions is not set forth here.

The present ligands can be produced from inexpensive and readily available materials, using chemical synthesis techniques which are well known in the art. To illustrate, many of the present ligands are derived from or based on pyrazole, and can be produced following one of two synthetic routes. In the first route pyrazole is converted to an electrophilic precursor, whereas in the second route the pyrazole precursor is the nucleophile.

Preparation of Electrophilic Pyrazole Precursor

Pyrazole 1 is converted into chloride 4 in accordance with the following reaction sequences:

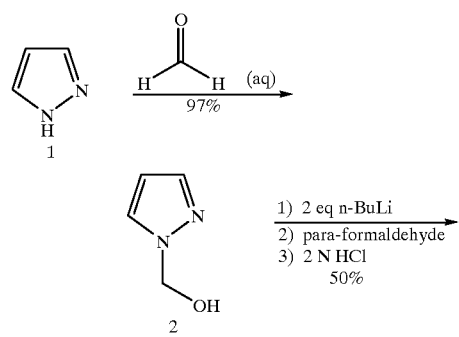

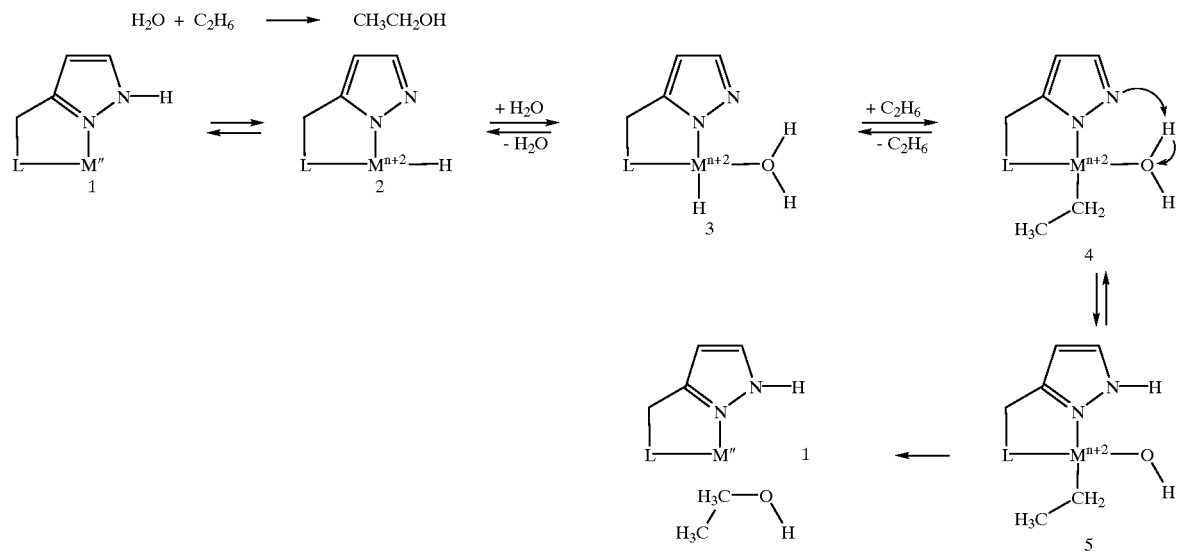

Similar reaction mechanisms can be envisioned for reactions of other alkenes or alkynes with water, alcohols, ammonia and amines These reactions are conducted by contacting the reactants together with the complex in accordance with the present invention at effective reaction conditions to obtain the desired product or products. Such reaction conditions can vary widely depending on many factors, such as the reactants and complex being employed, the concentrations of the reactants and complex, the desired product or products and other factors. However, such reac-

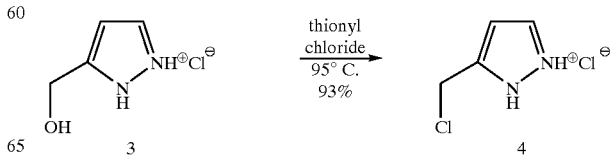

It has been found that an organic solvent is unnecessary in the first step or reaction and the yield of 2 exceeded 95%. Protected pyrazole 2 can then be lithiated with two equivalents of an alkyllithium, such as n-butyllithium, and the pyrazole moiety is than alkylated with formaldehyde. Subsequent deprotection in hydrochloric acid yielded 3. Alcohol 3 is then converted to chloride 4 with thionyl chloride, as noted above.

Use of the Electrophilic Pyrazole Precursor

The present ligands can be prepared in accordance with the following:

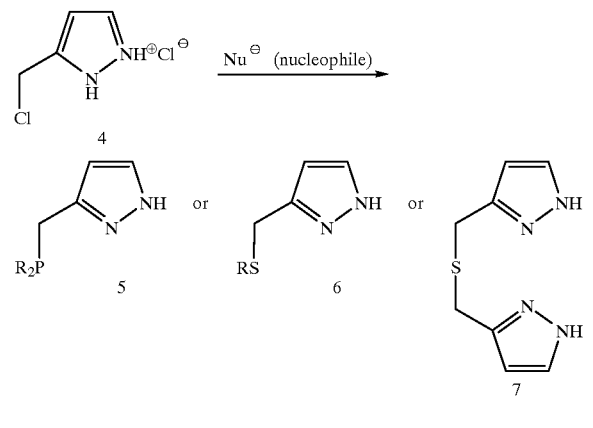

The desired ligand 5 can be obtained using three equivalents of lithium diphenylphosphide. Lithium thiomethoxide and sodium disulfide also can be used, giving ligands 6 and 7, respectively. Further, this synthetic route gives access to mono-pyrazole ligands with the general structure of 5 and 6 (bis-pyrazole)-ligands, such as 7. By changing the R substituent and the tethered ligating atom, a library of ligands with varying steric hindrances and electronic environments can be produced. In addition, solubility properties of the resulting metal complexes can be drastically altered with the use of thiols, such as commercially available 2-mercaptoethanesulfonic acid sodium salt or 2-mercaptoethanol.

Direct Alkylation of Nucleophilic Pyrazole Precursors

The pyrazole moiety as a carbon nucleophile can be used on electrophiles to obtain pyrazole-based ligands in a one pot synthesis. The Examples of such ligands include 9–11.

Direct Alkylation of Nucleophilic Pyrazole

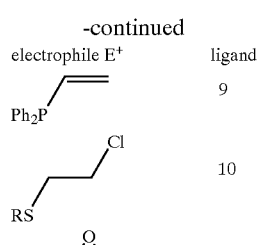

Preparation of Isoelectronic and Isosteric Pyrazole Ligands Incapable of Hydrogen Bonding and Proton Transfer Isoelectronic and isosteric ligands can be prepared according to a synthetic route illustrated below:

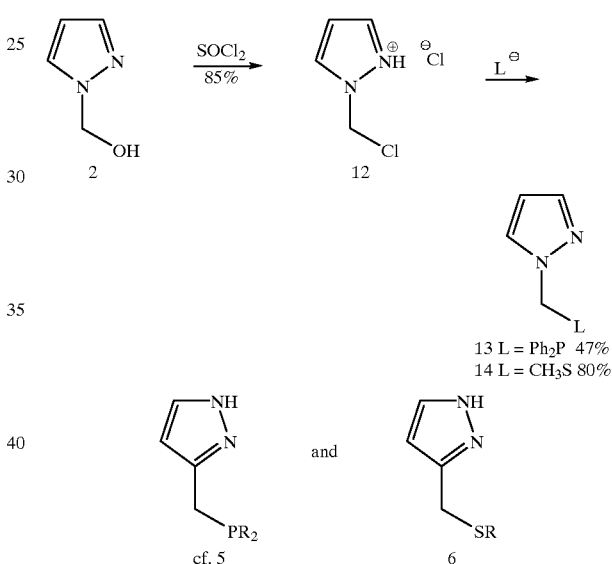

Compound 2 is converted to chloride 12, which can be used in the same way that isomer 4 is used. These ligands provide complexes not capable of hydrogen bonding when chelated to a metal through phosphorus and the unsubstituted nitrogen.

A range of transition metals with varying oxidation states can be complexed with the present ligands, for example, using the following general reaction scheme:

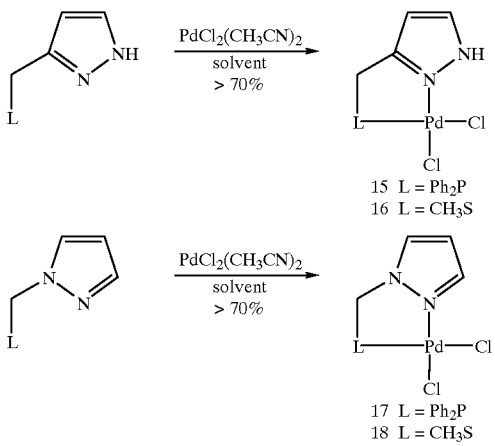

15 L = Ph₂P
16 L = CH₃S

17 L = Ph₂P
18 L = CH₃S

In one embodiment, the metal has an oxidation state which is unlikely to give complexes which oxidatively add the nitrogen-hydrogen bond of the pyrazole moiety. In addition, the formation of stereoisomeric products preferably is reduced. The metals selected preferably are those likely to give four-coordinate complexes. A specific example is palladium(II).

In another embodiment, the oxidation state and structural criteria described above are retained and, in addition, the metals are selected based on a change in the relative $pK_a$'s of their respective aquo-metal ions. Examples include metals such as platinum(II), zinc(II), and nickel(II), which have aquo-metal ions with $pK_a$'s of 4, 9 and 10, respectively, whereas the aquo-metal ion of palladium(II) has a pKa of 2.

Metals capable of making hexa or penta coordinated complexes may be employed. Examples include chromium, manganese, iron, cobalt, copper, zinc, molybdenum, ruthenium, rhenium, palladium, silver hafnium, tantalum, tungsten, rhodium, osmium, iridium, platinum and gold. Still more preferably, the transition metal moiety is a moiety of a metal selected from iron, cobalt, copper, zinc and palladium.

The complexes can be substituted with various ligands such as triflate, acetate, water or alcohol. These changes in the metal complexes allow adjusting the solubilities of the complexes to enable the hydrolysis of amides, phosphodiesters and nitriles and the addition to carbon dioxide to be conducted in polar or nonpolar solvents.

The present complexes are effective as hydrolysis reagents or reaction facilitators, such as catalysts. For example, it has been found that the complex 19, set forth below:

19

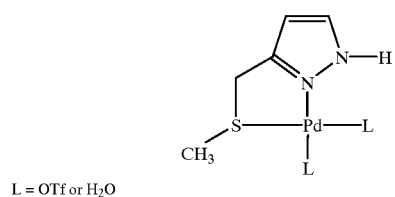

L = OTf or H₂O was catalytic toward the hydrolysis of N,N-dimethylacetamide and gave a more than 9% yield of the hydrolysis products. However, when complex 17 noted previously was used with dimethylformamide in acetonitrile and water at 75° C. amide cleavage products in 4% yield were provided while complex 20 set forth below:

20

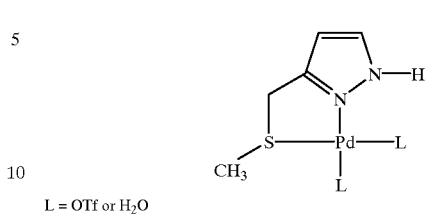

L = OTf or H₂O was found to be inactive. Although these reactions were slow and only 2 catalytic turnovers were achieved, these results are preliminary in nature. The conditions for the hydrolysis can be adjusted to provide enhanced results.

The following non-limiting examples illustrate certain aspects of the present invention.

EXAMPLE 1

Preparation of 3-(diphenylphosphinomethyl)pyrazole having the following structure:

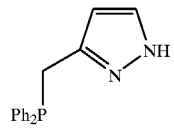

To a solution of tetrahydrofuran (100 ml) and triphenylphosphine (3.56 g, 13.6 mmol) at room temperature is added lithium (0.100 g, 14.5 mmol). The reaction mixture is stirred at room temperature for 2 hours at which time the lithium has dissolved. The bright red solution is cooled to 0° C., and 3-(chloromethyl)pyrazole hydrochloride (0.960 g, 6.8 mmol) is added at once. The ice bath is removed and the reaction solution is allowed to stir an additional 2 hours. Degassed ethanol (40 ml) is added to the reaction mixture followed by diethyl ether (100 ml). The organic phase is separated and the aqueous phase extracted with diethyl ether (2×25 ml). The organic phases are combined and dried over magnesium sulfate, filtered and concentrated. The crude residue is purified by chromatography (SiO₂, 50% ethyl acetate/petroleum ether) to give purified 3-(diphenylphosphinomethyl)pyrazole as a cloudy white oil in 77% yield (2.81 g, 10.6 mmol). This material is characterized as follows: ¹H NMR (CDCl₃, 500 MHz) δ 7.43 (m,4H), 7.41 (d, J=2.0 Hz, 1H), 7.34 (m, 6H), 5.99 (d, J=2.0 Hz, 1H), 3.47 (s, 2 H); ¹³C{¹H} NMR (CDCl₃, 125 MHz) δ 138.16 (d, 14.3 Hz), 132.97 (d, J=18.6 Hz), 129.11, 128.73 (d, J=6.6 Hz), 105.18 (d, J=5.1 Hz), 27.14 (d, J=6.2 Hz) MS m/z 265.9, 182.9 (M-C₄H₃N₂).

EXAMPLE 2

Preparation of cis-Dichloro-[(η²-P,N)-3-(Diphenylphosphinomethyl)pyrazole]palladium(II) having the following structure:

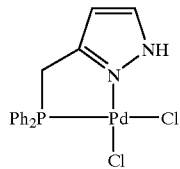

To 3-(diphenylphosphinomethyl)pyrazole (0.124 g, 0.46 mmol) and bis(acetonitrile)palladium(II) dichloride (0.121 g, 0.46 mmol) is added degassed methanol (10 ml). The reaction slurry is stirred 14 hours at room temperature. The reaction slurry is filtered and the solid is washed with petroleum ether (2×10 ml). The solid residue is placed under vacuum to give pure cis-dichloro-($\eta^2$-P,N)-3-[(diphenylphosphino-methyl)pyrazole] palladium(II) as a yellow solid in 93% yield (0.192 g, 0.43 mol). Crystals for X-ray analysis are grown with the slow evaporation of methanol from a solution. This material is characterized as follows: $^1$H NMR (DMSO-$d_6$, 200 MHz) δ 12.90 (s, 1 H), 7.88 (m, 5 H), 7.60 (m, 6 H), 6.54 (bs, 1 H), 4.03 (d, J=13 Hz, 2 H); $^{13}$C{$^1$H} NMR (DMSO-$d_6$, 50 MHz) δ 152.38 (d, J=6.5 Hz), 134.09, 133.09 (d, J=11.0 Hz), 132.28 (d, J=3.1 Hz), 129.14 (d, J=11.8 Hz), 127.67 (d, J=55.4 Hz), 104.56 (d, J=12.9 Hz), 28.68 (d, J=31.9 Hz); $^{31}$P{$^1$H} NMR (DMSO-$d_6$, 80 MHz) δ 46.67; M/S FAB 439, 440, 441, 442, 443, 444, 445, 446, 447.

EXAMPLE 3

Preparation of 1-(Diphenylphosphinomethyl)pyrazole having the following structure:

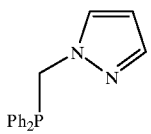

Diphenylphosphine (2.642 g, 14.2 mmol) is placed into a Schlenk flask with degassed tetrahydrofuran (50 ml). The solution is cooled to −78° C. and n-butyllithium (8.4 ml, 1.6 M in hexanes, 15.0 mmol) is added dropwise. The red solution is stirred at −78° C. for an additional 1 hour then the cooling bath is removed and the solution is stirred for 3 hours. The red solution is cooled to 0° C. and 1-(chloromethyl)pyrazole hydrochloride (0.698 g, 4.56 mmol) is added at once. The ice bath is removed and the reaction is stirred for 11 hours before adding degassed methanol (25 ml) and water (20 ml). The organic phase is separated and the aqueous phase is extracted with diethyl ether (3×10 ml). The organic phase is dried over magnesium sulfate, filtered and concentrated. The crude material is purified by chromatography (SiO$_2$, 10% ethyl acetate/petroleum ether) to give 1-(diphenylphosphinomethyl)pyrazole as a white solid in 47% yield (0.574 g, 2.16 mmol). This material is characterized as follows: $^1$H NMR (CDCl$_3$, 500 MHz) δ 7.49 (dd. J=2.0, 0.5 Hz, 1 H), 7.45–7.40 (m, 4 H), 7.40–7.35 (m, 6 H), 7.25 (dd, J=2.5, 0.5 Hz, 1 H), 6.19 (dd, J=2.5, 2.0 Hz, 1 H), 4,91 (d, J=4.5 Hz, 2 R); $^{13}$C{$^1$H} NMR (CDCl$_3$, 125 MHz) δ 139.50, 136.04 (d, J=13.4 Hz), 133.18 (d, J=19.3 Hz), 129.34, 129.49, 128.95 (d, J=6.4 Hz), 106.11, 53.01 (d, J=16.0 Hz); $^{13}$P{$^1$H} NMR (CDCl$_3$, 80 MHz) δ−14.98.

EXAMPLE 4

Preparation of cis-Dichloro-[($\eta^2$-P,N)-1-(Diphenylphosphinomethyl)pyrazole]palladium(II) having the following structure:

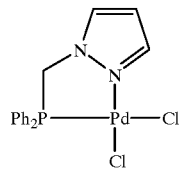

A flask is charged with 1-(diphenylphosphinomethyl)pyrazole (0.049 g, 0.184 mmol) and bis(acetonitrile) palladium(II) dichloride (0.048 g, 0.186 mmol). Degassed methanol (5 ml) is added. The resulting yellow solution instantaneously becomes cloudy. The slurry is stirred for 5 hours at room temperature then filtered through a glass frit. The precipitate is washed with dichloromethane then dried under vacuum (0.05 mmHg) giving cis-dichloro-[($\eta^2$-P,N)-1-(diphenylphosphinomethyl)pyrazole] palladium(II) (0.068 g, 0.153 mmol) in 83% yield. This material is characterized as follows: $^1$H NMR (DMSO-$d_6$, 200 MHz) δ 8.24 (m, 1 H), 8.09 (m, 1 H), 8.00–7.80 (m, 4 H), 7.75–7.40 (m, 6 H), 6.61 (m, 1 H), 5.47 (d. 8.2 Hz).

EXAMPLE 5

Preparation of 3-(Methylthiomethyl)pyrazole having the following structure:

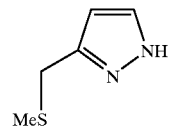

3-(Chloromethyl)pyrazole hydrochloride (1.77 g, 11.6 mmol) is dissolved in dried tetrahydrofuran (100 ml) under nitrogen atmosphere. At room temperature, MeSLi (1.25 g, 2.32 mmol) is added to the mixture. The solution becomes slightly pink. The reaction is stirred for 10 hours and quenched with water (3 ml). Then the solvent is distilled off by rotary evaporation. The organic phase is extracted with ethyl acetate (3×10 ml). The organic phases are combined, dried over magnesium sulfate, filtered and concentrated. The crude residue is purified by Kugelrohr distillation at 140° C./0.5 mmHg to give 3-(methylthiomethyl)pyrazole as a clear oil in 82% yield (1.22 g, 9.52 mmol). This material is characterized as follows: $^1$H (CDCl$_3$, 500 MHz) δ 9.2 (broad, 1 H), 7.55 (d, J=2.0 Hz, 1 H), 6.24 (d, J=2.0 Hz, 1 H), 3.77 (s, 2H), 2.06 (s, 3H) ppm. $^{13}$C (CDCl$_3$, 500 MHz) δ 146.31 (broad), 132.85, 104.78, 30.08, 15.42 ppm. FT-IR (NaCl, cm$^{-1}$) 3519, 2886, 1467, 1340, 1105.

EXAMPLE 6

Preparation of Cis-Dichloro-[($\eta^2$-S, N)-(3-methylthiomethyl)pyrazole]palladium(II) having the following structure:

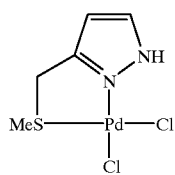

To a solution of 3-(methylthiomethyl)pyrazole (0.67 g, 5.25 mmol) in methanol (10 ml) under nitrogen atmosphere at room temperature is added $PdCl_2$ (1.36 g, 5.25 mmol). The Pd complex dissolves in about 5 minutes with stirring. The reaction is stirred for 12 hours, during which time orange solid forms The reaction mixture is filtered, and the solid is washed with methanol (2×5 ml). The solid residue is placed under vacuum to give pure cis-dichloro-[($\eta^2$-S,N)-(3-methylthiomethyl)pyrazole]palladium(II) in 80% yield (1.36 g, 4.46 mmol). This material is characterized as follows: $^1$H (DMSO-$d_6$, 500 MHz) δ 12.5 (a, 1H), 7.89 (d, J=2.0 Hz, 1H), 6.54 (d, J=2.0 Hz, 1H), 4.31 (d, J=16.5 HZ, 1H), 3.99 (d, J=16.5 Hz, 1H), 2.62 (s, 3H) ppm. $^{13}$C (DMSO-$d_6$ 500 MHz) δ 154.92, 133.44, 104.61, 35.06, 23.15 ppm. FT-IR (KBr, cm$^{-1}$) 3493, 3309, 2921, 1516, 1422, 1375.

EXAMPLE 7

Preparation of the compound having the following structure:

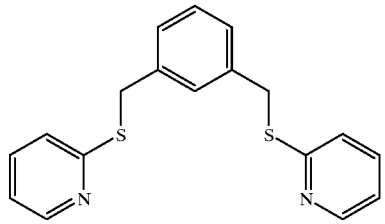

To a stirred suspension of NaH (65.4 mg of 80% suspension in mineral oil, 2.18 mmol) in dry N,N-dimethylformamide (2 ml) in an ice-cooled Schlenk flask is added 2-mercaptopyridine in two portions (221.0 mg, 1.99 mmol). Bubbling is noted. After 1 minute the ice bath is removed After another 2 minutes the ice bath is returned, and after 4 minutes solid α, α'-dibromo-m-xylene (256.5 mg, 0.972 mmol) is added in one portion, dissolving within 0.5 minutes. Within 2 minutes the mixture becomes too thick to stir, and the ice bath is removed. After 2.5 hours a solution of water and sat. aq. $NaHCO_3$ (10 ml each) is added to the mixture. The resulting cloudy mixture is extracted with $CH_2Cl_2$(3×10 ml) and ethyl acetate 3×10 ml). The combined organic extracts are washed with water (1×10 ml), brine (1×10 ml), and dried over $MgSO_4$ and filtered. The aqueous washes were back-extracted with ethyl acetate (1×10 ml). The combined filtrates are concentrated by rotary evaporation leaving slightly cloudy yellowish oil (574.9 mg) which is purified by radial chromatography using a 4 mm thick $SiO_2$ plate and ethyl acetate-petroleum ether mixtures. Product-containing fractions are concentrated by rotary evaporation, the residue is swirled with petroleum ether and concentrated. After storage on the high-vacuum line, product remains as colorless oil (302.5 mg, 96% yield). This material is characterized as follows: $^1$H NMR (CDCl$_3$, 500 MHz) δ 8.45 (ddd, J=1.0, 2.0, 5.0 Hz, 2H, pyridine H-6), 7.46 (ddd, J=1.9, 7.4, 8.1 Hz, 2H, pyridine H-4), 7.46 (s, 1 H), 7.29 (dd, J=1.6. 7 Hz, 2H), 7.22 (dd, J=6.7, 8.4 Hz, 1 H), 7.15 (td, J=1.0, 8.1 Hz, 2H, pyridine H-3), 6.98 (ddd, J=1.1, 5.0, 7.4 Hz, 2 H), 4.42 (s, 4 H) ppm. $^{13}$C{$^1$H} NMR (CDCl$_3$, 125 MHz) δ 158.72, 149.35, 138.15, 135.89, 129.57, 128.59, 127.69, 122.04, 119.53, 34.27 ppm. Analysis calculated for: $C_{18}M_{16}N_2S_2$; C, 66.63; M, 4.97; N, 8.63. Found: C, 66.67; H, 4.88; N, 8.58.

EXAMPLE 8

Preparation of the palladium(II) complex of the product of Example 7.

The product of Example 7 is stirred with palladium(II) acetate or trifluoroacetate in a solvent such as dichloromethane, chloroform, methanol, or toluene at a temperature and for a time needed to produce the desired palladium(II) complex. Alternatively, tetrakis(acetonitrile) palladium(II) trifluoromethanesulfonate is used.

The desired complex can also be made in accordance with the following reaction scheme.

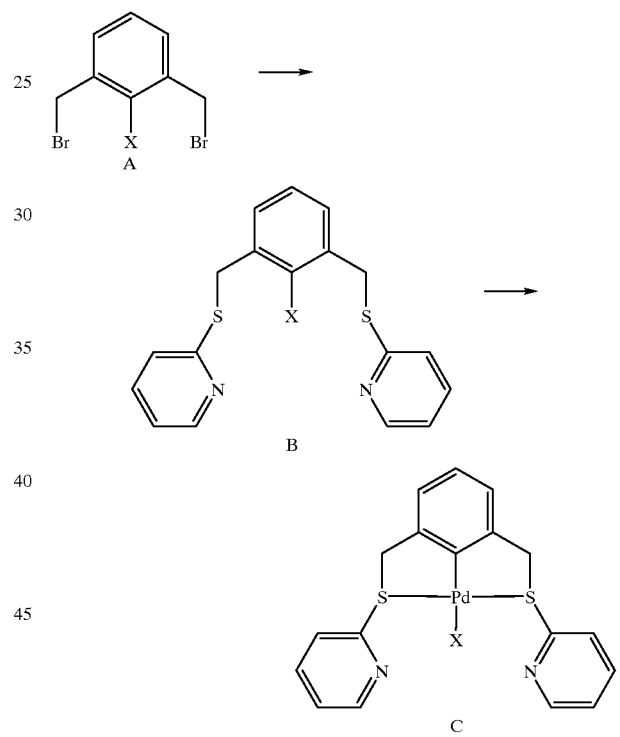

A solution of α, α',2-tribromo-m-xylene (compound A,X=Br) in an appropriate organic solvent such as N,N-dimethylformamide or acetonitrile or mixture of solvents is treated with a solution made from 2-mercaptopyridine and a suitable base, such as sodium hydride or potassium t-butoxide, in an appropriate organic solvent or mixture of solvents. After an appropriate time at an appropriate temperature (e.g. 1 hour at 25° C.), the mixture is worked up to isolate product B. Other 2-functionalized α,α'-dibromo-m-xylenes can also be used.

The product B mixed with an appropriate palladium complex such as tetrakis(triphenylphosphine)palladium(O), tris(benzylideneacetone)dipalladium(O), palladium(II) acetate or trifluoroacetate, bis(acetonitrile)palladium(II) trifluoromethanesulfonate with or without other additives such as phosphines, amines, inorganic bases or acetonitrile in an appropriate solvent such as acetonitrile, dichloromethane, chloroform, methanol, or toluene at a temperature and for a time needed to produce the desired palladium(II) complex C.

EXAMPLE 9

Preparation of 2,6-Pyridine dicarboxamide, N,N'-bis(2-pyridinyl) having the following structure:

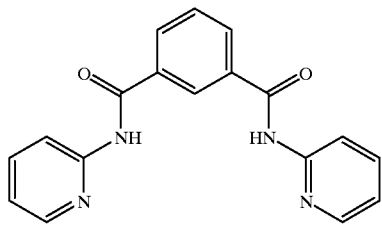

A solution of 2,6-pyridine dicarbonyl dichloride (4.34 g, 21.2 mmol) and 4-dimethylamino-pyridine (0.259 g, 2.12 mmol) in methylene chloride (10 ml) is prepared under nitrogen. In a separate flask, a solution of 2-aminopyridine (4.00 g, 42.4 mmol) and triethylamine (5.77 ml, 42.4 mmol) in methylene chloride (10 ml) is prepared. The aminopyridine solution is added over 10 minutes to the pyridine dicarbonyl dichloride while stirring and refluxing. This causes the solution to change from colorless to light green with a white precipitate. After refluxing the reaction for 3 hours, the mixture is cooled and the precipitate filtered, and washed with cold methanol (3×5 ml). The brown filtrate is then washed with water (3×10 ml). After washing the aqueous extract once with methylene chloride (5 ml), the combined organic layer is stripped of solvent and the resulting solid is recrystallized from pyridine as white needles (4.81 g, 71% yield). This material is characterized as follows:

$^1$H NMR (CDCl$_3$, 200 MHz) δ 11.08 (s, 2H), 8.53 (d, J=8 Hz, 2H), 8.40 (d, J=3.8 Hz, 2H), 8.17 (t, J=7.5 Hz, 1H), 7.82 (t, J=7 Hz, 2H), 7.13 (t, J=6.9 Hz, 2H); $^{13}$C (CDCl$_3$, 50 MHz) δ 160.46, 149.90, 147.20, 146.28, 137.97, 137.24, 124.26, 118.57, 113.04.

EXAMPLE 10

Preparation of palladium(II) complex of product of Example 9.

The product of Example 9 is stirred with a palladium(II) complex such as palladium(II) acetate, or trifluoroacetate, or bis(acetonitrile)palladium(II) dichloride, or tetrakisa (acetonitrile)palladium(II) trifluoromethanesulfonate in a solvent such as dichloromethane, chloroform, methanol, or toluene at a temperature and for a time needed to produce the desired palladium(II) complex.

EXAMPLE 11

Preparation of 2,6-pyridine dicarboxamide, N,N'-bis(2-methyl-6-pyridinyl) having the following structure:

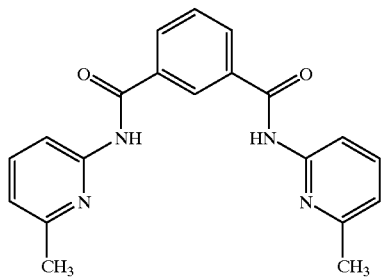

A solution of 2,6-pyridine dicarbonyl dichloride (4.34 g, 21.2 mmol) and 4-dimethylamino-pyridine (0.259 g, 2.12 mmol) in methylene chloride (10 ml) is prepared under nitrogen. In a separate flask, a solution of 2-amino-6-picoline (4.58 g, 42.4 mmol) and triethylamine (5.77 ml, 42.4 mmol) in methylene chloride (10 ml) is prepared. The aminopicoline solution is added over 10 minutes to the pyridine dicarbonyl dichloride while stirring and refluxing. After refluxing the reaction for 3 hours, the precipitate is filtered, and washed with cold methanol (3×5 ml). The brown filtrate is then washed with water (3×10 ml) After washing the aqueous extract once with methylene chloride (5 ml), the combined organic layer is stripped of solvent and the resulting solid is recrystallized from pyridine as white needles (6.47 g, 88% yield). This material is characterized as follows:

$^1$H NMR (CDCl$_3$, 200 MHz) δ 11.15 (s, 2H), 8.50 (d, J=7.6 Hz, 2H), 8.33 (d, J=8.2 Hz, 2H), 8.14 (t, J=7.7 Hz, 1H), 7.70 (t, J=7.9 Hz, 2H), 6.98 (d, J=7.4, 2H), 2.56 (s, 6H); $^{13}$C (CDCl$_3$, 50 MHz) δ 159.78, 147.56, 137.82, 133.12, 128.08, 123.82, 118.92, 19.27.

EXAMPLE 12

Preparation of palladium(II) complex of product of Example 11.

The product of Example 11 is stirred with a palladium(II) complex such as palladium(II) acetate or trifluoroacetate, or bis(acetonitrile)palladium(II) dichloride, or tetrakis (acetonitrile)palladium(II) trifluoromethanesulfonate in a solvent such as dichloromethane, chloroform, methanol, or toluene at a temperature and for a time needed to produce the desired palladium(II) complex.

EXAMPLE 13

Hydrolysis of N,N-dimethylacetamide using cis-dichloro-[η$^2$-S,N-(3-methylthiomethyl)pyrazole]palladium(II) (Product of Example 6).

Cis-dichloro-[η$^2$-S, N)-(3-methylthiomethyl)pyrazole] palladium(II) (0.30 9, 1.0 mmol) is dissolved in N,N-dimethylacetamide (1.74 g, 20 mmol) at room temperature. Silver triflate (0.52 g, 2.0 mmol) is added to the solution. Cloudy precipitation results, and the reaction mixture is centrifuged. The yellow solution is transferred by pipet into a small vial and diluted with D$_2$O (1.2 g, 60.0 mmol). The reaction mixture is stirred for 2 hours. The first aliquot is taken for analysis by NMR spectroscopy. No peaks of hydrolysis products are observed. The pH is also observed to be around 3.6–4.0. Then the reaction mixture is heated to 75° C. After 1 day at 75° C., 8.7% of hydrolysis products are observed in an analysis of a second aliquot by NMR spectroscopy. After 5 days of heating at 75° C., 8.6% of hydrolysis products are observed by NMR spectroscopy.

The pH is also observed to be around 3.6–4.0. The reaction mixture is heated to 90° C., and 9.4% of hydrolysis products are observed. Then triflic acid is slowly added into the mixture reaction until the pH is at 1–2. The mixture reaction is heated to 75° C. 2.5 hours after adding the acid, 21.5% of hydrolysis is observed. The mixture is heated further at 75° C., but no further hydrolysis is observed.

Control Experiments. At pH 3.5–4.0: N,N-Dimethylacetamide (11.9 mg, 1.37 mmol) is mixed with $D_2O$ (624 mg, 31.2 mmol). Then trifluoromethanesulfonic acid is added into the reaction mixture until pH is measured as 3.5–4.0. The reaction mixture is heated to 75° C. After 2 and 4 days, no hydrolysis products are observed by NMR spectroscopic analysis of the mixture. At neutral pH: N,N-Dimethylacetamide (4.87 mg, 0.56 mmol) is mixed with $D_2O$ (600 mg, 30.0 mmol). The reaction mixture is heated to 85° C. After 8 days, no hydrolysis is observed. Then the reaction mixture is heated to 90° C., and after 21 days, no hydrolysis is observed.

EXAMPLE 14

Hydrolysis of phosphate ester using cis-dichloro-[$\eta^2$-S,N)-(3-methylthiomethyl)pyrazole]palladium(II) (Product of Example 6).

The product of Example 6, with or without other additives including silver or thallium salts, acids, or bases, is combined with a phosphate ester, such as DNA or RNA, in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the phosphate ester to the desired degree.

EXAMPLE 15

Hydrolysis of nitrile component using cis-dichloro-[($\eta^2$-S,N)-3-methylthiomethyl)]pyrazole palladium(II) (Product of Example 6).

The product of Example 6, with or without other additives including silver or thallium salts, acids, or bases, is combined with a nitrile component, such as acetonitrile, in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the nitrile component to the desired degree.

EXAMPLE 16

Hydrolysis of cyanide ion-containing component using cis-dichloro-[($\eta^2$-S,N)-(3-methylthiomethyl)pyrazole]palladium(II) (Product of Example 6).

The product of Example 6, with or without other additives including silver or thallium salts, acids, or bases, is combined with a cyanide ion-containing component in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the cyanide ion-containing component to the desired degree.

EXAMPLE 17

Conversion of carbon dioxide using cis-dichloro-[($\eta^2$-S,N)-(3-methylthiomethyl)pyrazole]palladium(II) (Product of Example 6).

The product of Example 6, with or without other additives including silver or thallium salts, acids, or bases, is combined with other reactants, such as alcohols (e.g. methanol) or amines (e.g., dimethylamine) in an appropriate solvent, such as a mixture of water and an organic co-solvent or an organic solvent or mixture of organic solvents. Carbon dioxide is introduced into the mixture and using the appropriate temperature, such as about 0° C. to about 100° C., and sufficient time, such as about 1 hour to about 36 hours, the desired conversion of carbon dioxide is obtained.

EXAMPLE 18

Alcoholysis of an amide using cis-dichloro-$\eta^2$-S,N-(3-methylthiomethyl)pyrazole palladium(II) (Product of Example 6).

The product of Example 6, with or without other additives including silver or thallium salts, acids, or bases, is combined with an amide, such as dimethylacetamide, and an alcohol, such as methanol, with or without the use of an appropriate so-solvent, such as excess alcohol or other organic solvent or mixture of organic solvents. The resulting mixture is allowed to react at an appropriate temperature, such as about 0° C. to about 100° C., for a sufficient time, such as 1 hour to about 96 hours, thereby providing alcoholysis of the amide to the desired degree.

EXAMPLE 19

Aminolysis of an amide using cis-dichloro-$\eta^2$-S,N-(3-methylthiomethyl)pyrazole palladium(II) (Product of Example 6)

The product of Example 6, with or without other additives including silver or thallium salts, acids, or bases, is combined with an amide, such as acetamide, and an amine, such as dimethylamine, with or without the use of an appropriate co-solvent, such as excess amine or other organic solvent or mixture of organic solvents. The resulting mixture is allowed to react at an appropriate temperature, such as about 0° C. to about 100° C., for a sufficient time, such as 1 hour to about 96 hours, thereby providing aminolysis of the amide to the desired degree.

EXAMPLES 20 TO 26

Examples 13 to 19 are repeated except that the product of Example 2 is used in place of the product of Example 6.

EXAMPLES 27 TO 33

Examples 13 to 19 are repeated except that the product of Example 4 is used in place of the product of Example 6.

EXAMPLES 34 TO 40

Examples 13 to 19 are repeated except that the product of Example 8 is used in place of the product of Example 6.

EXAMPLES 41 TO 47

Examples 13 to 19 are repeated except that the product of Example 10 is used in place of the product of Example 6.

EXAMPLES 48 TO 54

Examples 13 to 19 are repeated except that the product of Example 12 is used in place of the product of Example 6.

While this invention has been described with respect to various specific examples and embodiments, it is to be understood that the invention is not limited thereto and that it can be variously practiced within the scope of the following claims.

What is claimed is:

1. A complex comprising:
   at least one organic ligand including a first hetero atom and a second hetero atom directly bonded to the first hetero atom or located one carbon atom away from the first hetero atom, at least one of the first and second hetero atoms being nitrogen, and at least one additional hetero atom; and
   a transition metal moiety partially complexed by the organic ligand, the organic ligand being selected from the group consisting of

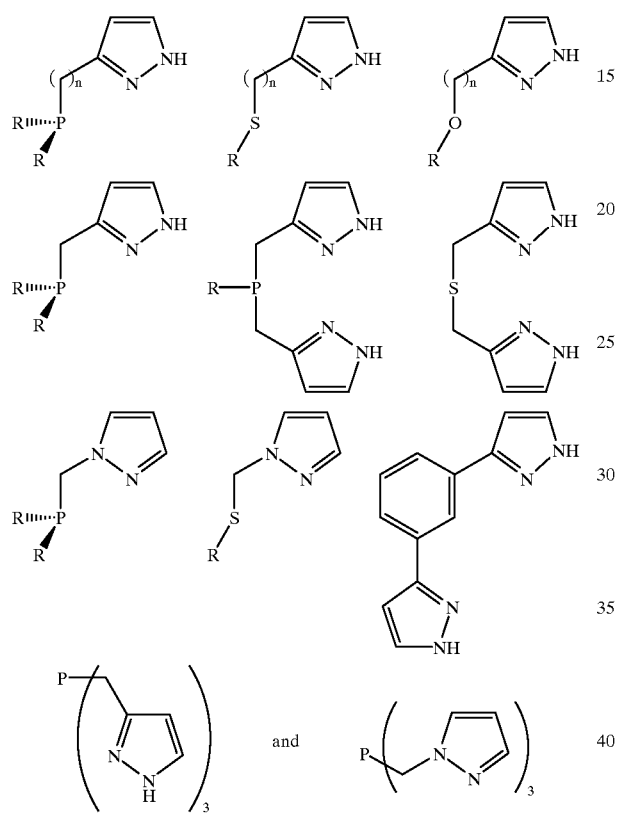

wherein n is an integer independently selected from 1 or 2, and each R is independently selected from monovalent radicals.

2. The complex of claim 1 wherein only one of the first hetero atom and the second hetero atom is directly bonded to the transition metal moiety and the other of the first and second hetero atoms is not directly bonded to another transition metal moiety or is not directly bonded to a carbon atom outside a heterocycle, or is directly bonded to H.

3. The complex of claim 2 wherein an additional hetero atom is bonded to a carbon atom of a heterocycle.

4. The complex of claim 2 wherein the other of the first and second hetero atoms is directly bonded to H.

5. The complex of claim 2 wherein the other of the first and second hetero atoms is not directly bonded to another transition metal moiety and is directly bonded to H.

6. The complex of claim 2 wherein the second hetero atom is located one carbon atom away from the first hetero atom.

7. The complex of claim 2 wherein the transition metal moiety is a moiety of a metal selected from the group consisting of Group IB metals, Group IIB metals, Group IIIB metals, Group IVB metals, Group VB metals, Group VIB metals, Group VIIB metals and Group VIIIB metals.

8. The complex of claim 2 wherein the transition metal moiety is a moiety of a metal selected from the group consisting of chromium, manganese, iron, cobalt, nickel, copper, zinc, molybdenum, ruthenium, rhenium, palladium, silver, hafnium, tallium, tungsten, rhodium, osmium, iridium, platinum and gold.

9. The complex of claim 2 wherein the transition metal moiety is a moiety of a metal selected from the group consisting of iron, cobalt, nickel, copper and palladium.

10. A method for producing a hydrolysis product comprising:
    contacting a reactant to be hydrolyzed in the presence of the complex of claim 1 in an amount effective to facilitate the hydrolysis of the reactant to the hydrolysis product, the contacting occurring at effective hydrolysis conditions, thereby forming the hydrolysis product.

11. The method of claim 10 wherein the reactant to be hydrolyzed is selected from the group consisting of compounds including amide bonds, nitrites, phosphoric acid esters and cyanide ions.

12. A complex comprising:
    at least one organic ligand selected from the group consisting of:

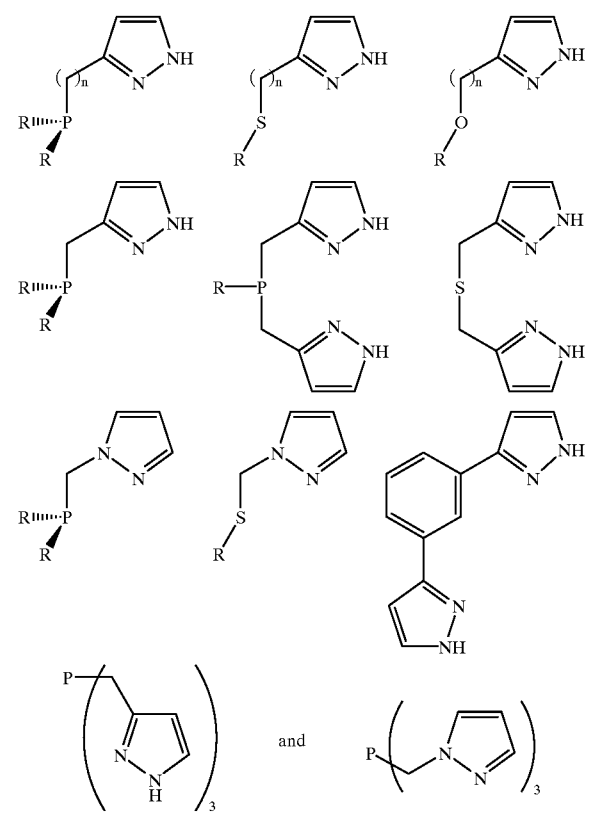

wherein n is an integer independently selected from 1 or 2, and each R is independently selected from monovalent radicals; and
    a transition metal moiety partially complexed by the organic ligand, wherein the transition metal moiety is a moiety of a metal selected from the group consisting of chromium, manganese, iron, cobalt, nickel, zinc, molybdenum, ruthenium, rhenium, palladium, silver, hafnium, tallium, tungsten, rhodium, osmium, iridium, platinum and gold.

13. The complex of claim 12 wherein only one of the first hetero atom and the second hetero atom is directly bonded to the transition metal moiety and the other of the first and second hetero atoms is not directly bonded to another transition metal moiety or is not directly bonded to a carbon atom outside a heterocycle, or is directly bonded to H.

14. The complex of claim 13 wherein the additional hetero atom is bonded to a carbon atom of the heterocycle.

15. The complex of claim 13 wherein the other of the first and second hetero atoms is directly bonded to H.

16. The complex of claim 13 wherein the other of the first and second hetero atoms is not directly bonded to another transition metal moiety and is directly bonded to H.

17. The complex of claim 13 wherein the second hetero atom is located one carbon atom away from the first hetero atom.

18. The complex of claim 12 wherein the transition metal moiety is a moiety of a metal selected from the group consisting of iron, cobalt, nickel, copper and palladium.

19. A method for producing a hydrolysis product comprising:
   contacting a reactant to be hydrolyzed in the presence of the complex of claim 12 in an amount effective to facilitate the hydrolysis of the reactant to the hydrolysis product, the contacting occurring at effective hydrolysis conditions, thereby forming the hydrolysis product.

20. The method of claim 19 wherein the reactant to be hydrolyzed is selected from the group consisting of compounds including amide bonds, nitrites, phosphoric acid esters and cyanide ions.

* * * * *